United States Patent [19]

Fujii et al.

[11] 4,207,312
[45] Jun. 10, 1980

[54] STABLE AQUEOUS SOLUTIONS OF GLUCANS AND GLUCAN DERIVATIVES CAPABLE OF INHIBITING SARCOMA IN MICE

[75] Inventors: Mitsuharu Fujii, Ageo; Tatsuo Kuoka, Iwatsuki; Tatsuo Setsuta, Tokyo; Yutaka Iwao, Urawa; Yasumi Yugari; Tsuyoshi Shiio, both of Kamakura; Takashi Yoshihama, Yokohama; Junji Hamuro, Tokyo, all of Japan

[73] Assignees: Ajinomoto Co. Ltd., Tokyo; Morishita Pharmiceuticals Co. Ltd., Osaka, both of Japan

[21] Appl. No.: 654,452

[22] Filed: Feb. 2, 1976

[30] Foreign Application Priority Data

Feb. 5, 1975 [JP] Japan .................................. 50-15788

[51] Int. Cl.$^2$ ...................... A61K 31/70; A61K 31/00
[52] U.S. Cl. ...................................... 424/180; 424/176
[58] Field of Search ................................ 424/180, 176

[56] References Cited

U.S. PATENT DOCUMENTS

3,987,166  10/1976  Komatsu et al. ..................... 424/180

FOREIGN PATENT DOCUMENTS

535471  1/1957  Canada ..................................... 424/227

OTHER PUBLICATIONS

American Hospital Formulary Service, 1966, p. 10.00, Testolactone.
Husa, Pharmaceutical Dispensing, 6th Ed., 1966, Mack Publishing Co. pp. 212, 213, 293 & 400.
Chemical Abstracts 74: 91107g (1971).
Chemical Abstracts 74: 110212f (1971).
Chemical Abstracts 79: 142893y (1973).
The Merck Index, 8th Ed., 1968, Merck & Co., Inc., Rahway, N.J., pp. 210 & 956.

*Primary Examiner*—Jerome D. Goldberg
*Attorney, Agent, or Firm*—Toren, McGeady and Stanger

[57] ABSTRACT

The glucans and glucan derivatives which inhibit the growth of sarcoma 180 in mice are only sparingly soluble in water, and their aqueous solutions are unstable. In the presence of 0.1 to 1.0 g/dl water soluble dextran, hydroxyethyl starch, carboxymethyl cellulose, or polyethylene glycol, they form relatively concentrated and stable solutions, particularly in the presence of hexoses, pentoses or sugar alcohols having 5 or 6 carbon atoms.

1 Claim, No Drawings

STABLE AQUEOUS SOLUTIONS OF GLUCANS AND GLUCAN DERIVATIVES CAPABLE OF INHIBITING SARCOMA IN MICE

This invention relates to glucans and glucan derivatives capable of inhibiting sarcoma 180 in mice, and particularly to stable and relatively concentrated, aqueous solutions of such compounds whose tumor-inhibiting properties are due to the glucan moiety and which are soluble in water in amounts smaller than 100 mg/dl.

Numerous glucans and glucan derivatives inhibit the growth of sarcoma 180 in mice, but are poorly soluble in water and suffer degradation with concomitant loss of anti-tumor activity when solubilized by means of known adjuvants. Moreover, the known aqueous solutions are unstable, and the active agents are precipitated within a short time.

It is a primary object of this invention to provide aqueous solutions of such glucans and glucan derivatives whose concentration is greater than the solubility of the active agents in water, but which are stable in that they neither suffer a significant decrease in anti-tumor activity, nor form precipitates after extended storage.

We have found that small amounts, typically 0.1 to 1.0 g/dl, of water-soluble dextran, hydroxyethyl starch, carboxymethylcellulose, or polyethyleneglycol improve the solubility of the sarcoma-inhibiting glucans and glucan derivatives in water, and that the stability of the relatively concentrated solutions so obtained is further enhanced by the presence of 1 to 10 g/dl of a pentose, hexose, or of a sugar alcohol having 5 or 6 carbon atoms.

The compounds whose anti-tumor activity is due to a glucan backbone and which form relatively concentrated and stable aqueous solutions according to this invention include lentinan, a $\beta$-(1→3) glucan (Japanese patent publication No. 484/1974) whose solubility in water at room temperature is only 38 mg/dl. Even such dilute solutions form insoluble precipitates within a day or two. Lentinan readily dissolves in alkaline aqueous media, but it is rapidly hydrolyzed and loses its anti-tumor activity in the alkaline solution.

The effects of the solubilizing agents of the invention on lentinan will be apparent from the following Example.

EXAMPLE 1

500 g Fresh fruit bodies of Lentinus edodes were washed, homogenized in a Waring blender with approximately two liters water, and the slurry so obtained was kept boiling with agitation for 16 hours. After removal of insoluble matter by centrifuging, one liter of supernatant was obtained and was evaporated to approximately one third of its original volume in a vacuum. The concentrate was poured into about 400 ml ethanol, whereby a fibrous precipitate weighing about 50 g was formed. It was recovered by means of a screen, washed with ethanol, and dispersed in two liters water by homogenizing in a Waring blender for 5 minutes. A clear solution was obtained by further diluting with 20 liters water and stirring.

A 0.2 molar solution of cetyltrimethylammonium hydroxide was added dropwise until no further colorless precipitate formed. The precipitate was recovered by centrifuging, washed in ethanol, stirred 5 minutes at room temperature in 1.2 liters 20% acetic acid, and again recovered as a precipitate by centrifuging. The procedure was repeated in 1.2 liters 50% acetic acid at 0° C. The recovered precipitate was dissolved in aqueous 0.5 N sodium hydroxide solution, and the solution so obtained was deproteinized by Sevage's method. From the deproteinized solution, pure lentinan was precipitated, washed, and dried as is known in itself.

The lentinan so obtained was dispersed in distilled water by means of a homogenizer, and the dispersion was heated to obtain a saturated solution which was divided in ten batches. Additions were made to several batches as indicated below, and each batch was diluted to 100 ml containing 0.1 g lentinan with distilled water, filtered through a Millipore filter, and distributed into 100 glass vials which were then sealed and sterilized in steam for 30 minutes at 110° C. Vials showing formation of a precipitate were rejected at once, and the others were stored two months at 40°, 25°, or 0° C.

Batch No. 1 contained no additives. 80 Vials were rejected immediately after sterilizing because of the formation of precipitate. All remaining vials stored at 40° C. showed precipitates, about ⅔ of the vials stored at 25° C. were equally deflective and also ½ of those stored at 0° C.

Batch No. 2, in addition to lentinan, contained 5 g/dl glucose. 70 Vials showed a precipitate after sterilizing and about one half of the initially clear solutions developed precipitates after storage at each of the three selected temperatures.

Batch No. 3 contained 0.9 g/ldl NaCl as the sole additive which caused precipitation in all vials after sterilizing.

Batches Nos. 4, 5, and 6 contained 1 g/dl dextran 70, 1 g/dl hydroxyethyl starch (M.W. 200,000), and 1 g/dl carboxymethylcellulose sodium as respective primary solubilizing agents. Approximately 10 vials of batch No. 5 had to be rejected after sterilization and 20 vials each of batches Nos. 4 and 6. Storage at 40°, 25°, or 0° C. did not cause formation of a precipitate in any other vial of this group.

Batch No. 7 in addition to lentinan and 1 g/dl dextran 70 contained 0.9 g/dl NaCl. Ten vials had to be rejected after sterilizing, and 10%–20% of the vials passing the first inspection showed precipitates after storage at the three temperatures mentioned.

Batches Nos. 8 to 10 differed from Batches Nos. 4 to 6 by the presence of 5 g/dl glucose as a secondary solubilizing agent. No vial was found to contain a precipitate after sterilizing, and no precipitate formed during two months of storage at 40°, 25°, or 0° C.

The anti-tumor effects of freshly sterilized batches of lentinan and of batches stored 2 months at 40° C. were tested on groups of generally ten ICR-JCL mice which were injected subcutaneously with $3 \times 10^6$ cells of sarcoma 180 in 0.05 ml ascites in the right groin. 24 Hours after the tumor cell injection and daily thereafter for a total of ten days, the mice received intraperitoneal injections of lentinan solutions corresponding to 1 mg lentinan per kg body weight and day. After five weeks, the tumors were excised and weighed, and the average inhibition effect was calculated in percent by comparison with the weights of tumors recovered from a group of untreated controls. The number of complete regressions of the tumors also was noted. Batch No. 3 could not be tested nor Batch No. 1 after storage because clear solutions were not available. The other results are shown in Table 1.

Table 1

| Batch No. | Freshly Sterilized Inhib (n) | Freshly Sterilized Regress'n | Stored 2 months Inhib (n) | Stored 2 months Regression |
|---|---|---|---|---|
| 1 | 85.3 | 6/10 | — | — |
| 2 | 89.4 | 7/9 | 87.9 | 5/8 |
| 4 | 92.5 | 7/10 | 88.5 | 6/10 |
| 5 | 92.5 | 7/10 | 90.1 | 6/10 |
| 6 | 91.7 | 7/10 | 82.3 | 6/10 |
| 7 | 93.0 | 8/10 | 81.1 | 4/10 |
| 8 | 94.1 | 8/10 | 92.9 | 5/10 |
| 9 | 93.4 | 8/10 | 92.9 | 7/10 |
| 10 | 92.8 | 8/10 | 83.1 | 7/10 | p Corresponding results were obtained when polyethyleneglycol was used instead of the dextran, hydroxyethyl starch, or carboxymethyl cellulose, and glucose could be replaced without significant difference in the stabilizing effect by other hexoses, pentoses, and sugar alcohols having 5 or 6 carbon atoms, such as xylose, xylitol, or sorbitol. The amount of carboxymethylcellulose could be reduced to about 0.5 g/dl without impairing the stability of the lentinan solution while as little as 0.1 g/dl of the other primary solubilizing agents was adequate. The amount of the secondary solubilizing agent was chosen to produce an approximately isotonic solution, but approximately equally stable solutions were obtained over a range from 1 to 10 g/dl.

Other glucans and glucan derivatives benefit from the solubilizing agents of the invention in the same manner as lentinan as is illustrated by the following Examples.

EXAMPLE 2

Pachyman was extracted from Poria cocos Wolf with an alkaline aqueous liquid, oxidized, hydrogenated, and hydrolyzed in the manner described in Saishin Igaku Zasshi (Recent Medicine, Japan) 25 (1970)1043, to prepare pachymaran.

Solution No. 11 was prepared from 0.1 g/dl pachymaran and 1 g/dl dextran as in Example 1, and solution No. 12 additionally contained 5 g/dl glucose. These solutions were tested together with solutions Nos. 13–36, as will be described hereinbelow.

EXAMPLE 3

A culture medium containing 50 g glucose, 1 g ammonium sulfate, and 3 g yeast extract per liter distilled water was adjusted to pH 5.5, and 50 ml batches thereof were sterilized in respective 500 ml shaking flasks at 120° C. for 15 minutes. The batches were inoculated respectively with seed cultures of Coriolus hirsutus FERM P-1021, Deadoleopsis FERM P-1023, Phellinus nobustus NRRL 3993, Fomes mcgregorii FERM P-1030, Phlebia strigozo-zonata FERM P-1027, Polyporus mollis FERM P-1032, and Inonotus cuticoloris NRRL 3991 and kept at 25° C. with shaking for 120 hours. The several broths of each microorganism were combined and centrifuged to remove mycelia. 800 ml Supernatant was obtained and diluted with ethanol to 40% ethanol concentration, whereby a precipitate was formed which was recovered by centrifuging. It was purified three times by dissolution in water and precipitation with ethanol. The crude glucan so obtained was dissolved in 200 ml 0.5 N sodium hydroxide solution, precipitated with ethanol, centrifuged out, washed twice with 80% ethanol and then twice with 100% ethanol. After drying in a vacuum, crystalline glucans were obtained from the seven microorganisms in respective amounts of 1.2, 0.7, 0.35, 0.51, 0.15, 0.34, and 0.52 g.

Solutions No. 13 and 14 were prepared from 0.1 g/dl of the glucan of C.hirsutus with 1 g/dl dextran without and with 5 g/dl glucose as in Example 2, corresponding solutions Nos. 15 and 16 from the glucan of Deadoleopsis, Nos. 17 and 18 from the glucan of P.nobustus, Nos. 19 and 20 from the glucan of F.mcgregorii, Nos. 21 and 22 from the glucan of P.strigozo-zonata, Nos. 23 and 24 from the glucan of P. mollis, and Nos. 25 and 26 from the glucan of I.cuticoloris.

EXAMPLE 4

Fruit bodies of Pholiota nameko were extracted by means of an alkaline aqueous liquid, and a polysaccharide whose backbone consisted of glucose units connected by $\beta$-(1→3) bonds were recovered by fractional precipitation with ethanol substantially in the manner described in Example 3. Solutions Nos. 27 and 28 were prepared from the purified product, water, and dextran as in Example 2, solution No. 28 additionally containing glucose.

EXAMPLE 5

60 g $\beta$-Pachyman was dissolved in 2 liters aqueous 1.2% NaOH solution in a three-liter flask. The solution was stirred at 40° C. under a nitrogen blanket while 75 ml (1.5 mole) ethylene oxide was added. After 24 hours stirring, the mixture became gelatinous. It was neutralized to pH 7.0 with concentrated hydrochloric acid, and the precipitate formed thereby was recovered by centrifuging, washed by stirring in 5 liters 70% methanol, and again recovered by centrifuging. The washing procedure was repeated with 80% methanol, 90% methanol, and ultimately with absolute methanol. The washed product was filtered off, washed by suspension in 2 liters acetone, again filtered off and a dried in a vacuum at ambient temperature.

The glucan derivative so obtained was a white powder weighing 59.4 g. It showed a degree of substitution of 0.43, and was employed for preparing solutions Nos. 29 and 30 as in the preceding Examples. The freshly sterilized solutions when applied to five mice as described in Example 1 produced complete remission of the tumors in all five tested mice.

EXAMPLE 6

3 g of Pachymaran prepared as in Example 2 was dissolved in 80 ml isopropanol by vigorous stirring at room temperature. 8 ml Aqueous 30% sodium hydroxide solution and thereafter 3 g solid monochloracetic acid were added to the solution which was stirred three hours on a water bath at 40° to 45° C. and further stirred during cooling to ambient temperature. The precipitate formed was filtered off on a glass filter, added to 100 ml 70% methanol containing 5 ml glacial acetic acid, and stirred for ten minutes. It was then recovered, washed with three changes of 100 ml absolute methanol and finally with ether. After drying in a vacuum, 2.2 g colorless, pulverulent carboxymethyl-$\beta$-(1→3) glucan was obtained.

1 g Carboxymethyl-$\beta$-(1→3) glucan was dissolved in 10 ml 1 N NaOH solution, and 50 ml methanol was added to the solution. The precipitate formed thereby was filtered off, washed sequentially with 70% methanol, 90% methanol, absolute methanol, and acetone, and dried. 0.8 g Sodium carboxymethyl-$\beta$-(1→3) glucan was obtained and employed for preparing solutions Nos. 31 and 32.

EXAMPLE 7

Coriolus hirsutus FERM P-1021 was cultured as described in Example 3, and the mycelium was recovered by centrifuging, washed, and dried. 10 g Dry mycelium was suspended in 200 ml 0.2 N sodium hydroxide solution, and the suspension was stirred vigorously at ambient temperature for two days and then centrifuged. The supernatant was adjusted to pH 6.5 with acetic acid whereafter 600 ml ethanol was added. The precipitate formed was recovered by centrifuging and sequentially washed with 70%, 80%, 90% methanol, absolute ethanol, acetone, and ether, and finally dried in a vacuum. The polysaccharide-protein complex so obtained weighed 810 mg and was employed for preparing solutions Nos. 33 and 34 in the manner outlined above.

EXAMPLE 8

Coriolus versicolor FERM P-1022 was cultured as in Example 3, and the mycelium was worked up as in Example 7 to produce a glucan-protein complex from which solutions Nos. 35 and 36 were prepared with dextran alone and with dextran and glucose respectively as in the preceding Examples.

EXAMPLE 9

When solutions Nos. 11 to 36 were sterilized, no precipitates were found in the even-numbered solutions which also contained glucose, and none developed in storage for two months at 40° C. Approximately 10% of the vials containing solutions Nos. 11, 15, 19, 23, 27, 29, and 31 were discarded after sterilization because of precipitate formation, and approximately 20% of the vials of solutions Nos. 13, 17, 21, 25, 33, and 35 were equally defective. The vials passing the first inspection were stored two months at 40° C. and again inspected. No precipitate could be detected in the vials containing solution No. 11, approximately 10% of the stored vials of solutions Nos. 13, 17, 19, 21, 23, 25, and 31 contained solid matter, and precipitates were found in approximately 20% of the stored vials of solutions Nos. 15, 27, 29, 33, and 35.

The clear, stored solutions were tested for their ability of inhibiting the growth of sarcoma 180 in Swiss albino mice in the manner described in Example 1. The dosage of active agent was 0.25, 0.5, or 1.0 mg/kg body weight in each injection as noted below in Table 2 which also lists the observed average inhibition and cases of total tumor remission together with the number of mice in the tested group.

Table 2

| Sol'n No. | Dosage mg/kg | Inhibition percent | Remission |
|---|---|---|---|
| 11 | 0.5 | 93 | 8/10 |
| 12 | 0.5 | 94 | 7/10 |
| 13 | 0.5 | 92 | 6/10 |
| 14 | 0.5 | 93 | 6/10 |
| 15 | 0.5 | 95 | 7/10 |
| 16 | 0.5 | 94 | 8/10 |
| 17 | 0.5 | 100 | 5/5 |
| 18 | 0.5 | 99 | 4/5 |
| 19 | 1.0 | 92 | 4/5 |
| 20 | 1.0 | 91 | 4/5 |
| 21 | 1.0 | 94 | 4/5 |
| 22 | 1.0 | 92 | 5/5 |
| 23 | 1.0 | 93 | 4/5 |
| 24 | 1.0 | 93 | 5/5 |
| 25 | 0.25 | 92 | 8/10 |
| 26 | 0.25 | 92 | 9/10 |
| 27 | 1.0 | 90 | 6/10 |
| 28 | 1.0 | 92 | 7/10 |
| 29 | 0.5 | 98 | 8/10 |
| 30 | 0.5 | 96 | 9/10 |
| 31 | 0.5 | 92 | 7/10 |
| 32 | 0.5 | 93 | 8/10 |
| 33 | 1.0 | 92 | 7/10 |
| 34 | 1.0 | 91 | 7/10 |
| 35 | 1.0 | 90 | 8/10 |
| 36 | 1.0 | 90 | 8/10 |

The glucans and glucan derivatives prepared in Examples 1 to 8 were also tested for toxicity to the mice when administered by intraperitoneal injection, and the $DL_{50}$ values of all tested compounds were found to be greater than 4,000 mg/kg.

The solubilizing agents of the invention have been found to be similarly effective in stabilizig relatively concentrated solutions of the anti-tumor agents recovered by extraction of fruit bodies or sclerotium of other basidiomycetes, from the mycelium of such basidiomycetes or of yeasts not specifically referred to in the preceding Examples, and from the culture broths of other fungi imperfecti. Schizophyllan recovered from the culture broth of Schyzophyllum commune, and anti-tumor glucans extracted from the fruit bodies of Flammulina velutipes, Pleurotus ostreatus, and Tricholoma matsutake are representative of such additional compounds effective in inhibiting sarcoma 180 in mice, whose solutions may be stabilized according to this invention.

The molecular weights of the anti-tumor compounds appear to be irrelevant for the purpose of this invention except for the limits inherent in the anti-tumor activity and the low solubility characteristic of the compounds.

While intraperitoneal injection is the most practical method of administering the solutions of the invention to mice, limited tests indicate that they are well tolerated by other warm-blooded laboratory animals when injected intravenously.

What is claimed is:

1. A stabilized solution consisting essentially of water, 0.1 g/dl of lentinan, 0 to 10 g/dl glucose, and water-soluble dextran, the amount of said dextran being 0.1 to 1.0 g/dl, and sufficient for increasing the solubility of said lentinan in water.

* * * * *